(12) United States Patent
Deuerlein et al.

(10) Patent No.: US 9,024,050 B2
(45) Date of Patent: May 5, 2015

(54) HYDROPHOBIC, FUNCTIONALIZED PARTICLES

(75) Inventors: Stephan Deuerlein, Ludwigshafen (DE); Imme Domke, Jersey City, NJ (US); Alexej Michailovski, Ludwigshafen (DE); Reinhold Rieger, Mutterstadt (DE); Piyada Charoensirisomboon, Mannheim (DE); David F. Blackwood, Long Valley, NJ (US); Christian Eichholz, Mannheim (DE); Robert Bayer, Sinsheim (DE); Dennis Loesch, Altrip (DE); Igor Shishkov, Mannheim (DE)

(73) Assignees: BASF SE, Ludwigshafen (DE); BASF Corporation, Florham Park, NJ (US)

( * ) Notice: Subject to any disclaimer, the term of this patent is extended or adjusted under 35 U.S.C. 154(b) by 83 days.

(21) Appl. No.: 13/434,176

(22) Filed: Mar. 29, 2012

(65) Prior Publication Data

US 2012/0264111 A1    Oct. 18, 2012

Related U.S. Application Data

(60) Provisional application No. 61/474,296, filed on Apr. 12, 2011.

(51) Int. Cl.
    *C07F 7/08* (2006.01)
    *H01F 1/00* (2006.01)

(52) U.S. Cl.
    CPC .............. *C07F 7/0836* (2013.01); *H01F 1/0054* (2013.01)

(58) Field of Classification Search
    CPC ........................... B01F 17/0078; H01F 1/0054
    USPC .................................................. 556/400, 463
    See application file for complete search history.

(56) References Cited

U.S. PATENT DOCUMENTS

| 2,886,460 | A | 5/1959 | Alexander et al. |
| 6,548,168 | B1 | 4/2003 | Mulvaney et al. |
| 2010/0239784 | A1 | 9/2010 | Owens |
| 2011/0127201 | A1 | 6/2011 | Domke et al. |
| 2011/0229384 | A1 | 9/2011 | Michailovski et al. |
| 2011/0272623 | A1 | 11/2011 | Domke et al. |
| 2011/0303772 | A1 | 12/2011 | Michailovski et al. |
| 2012/0058463 | A1 | 3/2012 | Deuerlein et al. |
| 2012/0125858 | A1 | 5/2012 | Hartmann et al. |
| 2012/0128930 | A1 | 5/2012 | Owens |

FOREIGN PATENT DOCUMENTS

| GB | 675188 | | 7/1952 | |
| WO | WO 99/21934 A1 | | 5/1999 | |
| WO | WO2004/037944 | * | 5/2004 | ............... C09K 3/18 |
| WO | WO 2006/105600 A1 | | 10/2006 | |
| WO | WO 2007/031775 A1 | | 3/2007 | |
| WO | WO 2009/059382 A1 | | 5/2009 | |

OTHER PUBLICATIONS

Sigma-Aldrich commercially-available ZnO composition (www.sigmaaldrich.com/catalog/product/sial/96479?lang=en&region=US, downloaded on Dec. 21, 2013).*
U.S. Appl. No. 13/306,454, filed Nov. 29, 2011, Imme Domke, et al.
International Search Report and Written Opinion issued Jul. 13, 2012, in PCT/EP2012/056555 filed Apr. 11, 2012 with English translation of category of cited documents.
U.S. Appl. No. 13/479,961, filed May 24, 2012, Stroefer, et al.
U.S. Appl. No. 13/509,413, filed May 11, 2012, Rieger, et al.
U.S. Appl. No. 13/504,519, filed Apr. 27, 2012, Rieger, et al.

* cited by examiner

*Primary Examiner* — Sudhakar Katakam
*Assistant Examiner* — Pancham Bakshi
(74) *Attorney, Agent, or Firm* — Oblon, McClelland, Maier & Neustadt, L.L.P.

(57) ABSTRACT

The present invention relates to a stable mixture comprising surface-modified particles which are obtained by reacting metal oxide or semimetal oxide particles with at least one compound selected from among silicon-comprising compounds bearing at least one metaloxy radical and optionally further alkoxy and/or hydroxy radical(s) and at least one solvent, at least one surface-active substance or a mixture thereof, a process for producing the mixture, the use of these particles in systems in which they are brought into contact with at least one solvent, where the mass ratio of solvent to modified particle is greater than 500, and also the use of these particles in agglomeration-deagglomeration cycles.

12 Claims, No Drawings

HYDROPHOBIC, FUNCTIONALIZED PARTICLES

The present invention relates to a stable mixture comprising surface-modified particles which are obtained by reacting metal oxide or semimetal oxide particles with at least one compound selected from among silicon-comprising compounds bearing at least one metaloxy radical and optionally further alkoxy and/or hydroxy radical(s) and at least one solvent, at least one surface-active substance or a mixture thereof, a process for producing the mixture, the use of these particles in systems in which they are brought into contact with at least one solvent, where the mass ratio of solvent to modified particle is greater than 500, and also the use of these particles in agglomeration-deagglomeration cycles.

Metal oxide and/or semimetal oxide particles which are functionalized on the surface by means of silicon-comprising compounds are known from the prior art.

WO 2009/059382 A1 discloses, for example, hydrophobic modification of mineral fillers and mixed polymer systems. According to this document, hydrophobic modification is effected by reaction of the corresponding mineral particles with silanes, for example $C_3$-$C_{12}$-alkyltrialkoxy silanes. That the correspondingly hydrophobically modified particles according to WO 2009/059382 A1 are particularly stable in large amounts of solvents, optionally in the presence of surface-active substances, is not disclosed in this document.

In the light of the prior art, it is thus an object of the present invention to provide particles which are hydrophobicized on the surface and have a particularly high stability toward large amounts of solvents and/or surface-active substances.

This object is achieved by a stable mixture comprising surface-modified particles which are obtained by reacting metal oxide or semimetal oxide particles with at least one compound of the general formula (I)

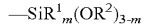

$$R^1{}_n\text{—Si}(OR^2)_{4-n} \qquad (I)$$

where $R^1$, $R^2$ and n have the following meanings:

the radicals $R^1$ are each, independently of one another, hydrogen, linear or branched, optionally functionalized $C_1$-$C_{30}$-alkyl, linear or branched, optionally functionalized $C_2$-$C_{30}$-alkenyl, linear or branched, optionally functionalized $C_2$-$C_{30}$-alkynyl, optionally functionalized $C_3$-$C_{20}$-cycloalkyl, optionally functionalized $C_3$-$C_{20}$-cycloalkenyl, optionally functionalized $C_1$-$C_{20}$-heteroalkyl, optionally functionalized $C_5$-$C_{22}$-aryl, optionally functionalized $C_6$-$C_{23}$-alkylaryl, optionally functionalized $C_6$-$C_{23}$-arylalkyl, optionally functionalized $C_5$-$C_{22}$-heteroaryl the radicals $R^2$ are each, independently of one another, hydrogen, linear or branched, optionally functionalized $C_1$-$C_{30}$-alkyl, linear or branched, optionally functionalized $C_2$-$C_{30}$-alkenyl, linear or branched, optionally functionalized $C_2$-$C_{30}$-alkynyl, optionally functionalized $C_3$-$C_{20}$-cycloalkyl, optionally functionalized $C_3$-$C_{20}$-cycloalkenyl, optionally functionalized $C_1$-$C_{20}$-heteroalkyl, optionally functionalized $C_5$-$C_{22}$-aryl, optionally functionalized $C_6$-$C_{23}$-alkylaryl, optionally functionalized $C_6$-$C_{23}$-arylalkyl, optionally functionalized $C_5$-$C_{22}$-heteroaryl, $NR^1{}_4{}^+$, where the radicals $R^1$ can, independently of one another, have the abovementioned meanings, a group of the general formula $1/(p-x*y)\, M^{p+}X^{x-}{}_y$, where M is a metal atom selected from the group consisting of metals of the main and transition groups of the Periodic Table of the Elements, X is an anion, p is the oxidation number of the metal atom M, x is 1, 2 or 3 and y is 0, 1 or 2, and/or a group of the general formula (IIa)

$$-\text{SiR}^1{}_m(OR^2)_{3-m} \qquad (IIa),$$

where $R^1$ and $R^2$ have, independently of one another, the abovementioned meanings and the indices m can be, independently of one another, 0, 1, 2 or 3, n is 1, 2 or 3, and at least one solvent, at least one surface-active substance or a mixture thereof, where at least one radical $R^2$ in the group of the general formula (IIa) is $NR^1{}_4{}^+$ or a group of the general formula $1/(p-x*y)\, M^{p+}X^{x-}{}_y$ with the abovementioned meanings of $R^1$, p, x, y, M and X.

If $R^2$ is a group of the general formula (IIa) a plurality of times, for example more than once, in the compound of the general formula (I), the corresponding compounds bear two, three, four or more units having Si atoms. Thus, when $R^2$ is a group of the general formula (IIa) a plurality of times, polysiloxanes are present.

Furthermore, the object is achieved by the use of the surface-modified particle according to the invention in systems in which the modified particles are brought into contact with at least one solvent, where the mass ratio of solvent to modified particle is greater than 500.

The object of the invention is also achieved by the use of surface-modified particles according to the invention in agglomeration-deagglomeration cycles.

The stable mixture of the invention comprises surface-modified particles which are obtained by reacting metal oxide or semimetal oxide particles with at least one compound of the general formula (I) or a polysiloxane of the general formula (I) comprising groups of the general formula (IIa).

For the purposes of the present invention, it is generally possible to use all metal oxide or semimetal oxide particles, in particular metal oxide particles, known to those skilled in the art. Examples of metal oxides which are particularly suitable for the purposes of the invention are the oxides of the metals of the main groups and transition groups of the Periodic Table of the Elements, in particular the transition groups of the Periodic Table of the Elements.

According to the invention, silicon oxide is not preferred as semimetal oxide and is therefore not comprised in a preferred embodiment of the present invention.

In a preferred embodiment, the present invention therefore provides the mixture according to the invention, with silicon dioxide being excepted as semimetal oxide.

Examples of suitable metals of the main groups of the Periodic Table of the Elements are the alkali metals, for example Li, Na, K, Rb, Cs, alkaline earth metals, for example Be, Mg, Ca, Ba, Sr, the third main group of the Periodic Table of the Elements, for example Al, Ga, In, Tl, the fourth main group of the Periodic Table of the Elements, for example Sn, Pb, or the fifth main group of the Periodic Table of the Elements, for example Sb, Bi.

Examples of suitable metals of the transition groups of the Periodic Table of the Elements are Sc, Y, the lanthanides, the actinides, Ti, Zr, Hf, Mn, Re, Fe, Ru, Os, Co, Rh, Ir, Ni, Pd, Pt, Cu, Ag, Au, Zn and Cd.

In a preferred embodiment, the metal oxide used according to the invention is an oxide of the metals selected from the group consisting of Li, Na, K, Rb, Cs, Be, Mg, Ca, Ba, Sr, Al, Ga, In, Tl, Sn, Pb, Sb, Bi, Sc, Y, the lanthanides, the actinides, Ti, Zr, Hf, Mn, Re, Fe, Ru, Os, Co, Rh, Ir, Ni, Pd, Pt, Cu, Ag, Au, Zn, Cd and mixtures thereof, very particularly preferably selected from the group consisting of Mn, Fe, Co, Ni, Cu and combinations thereof. Furthermore, mixed oxides of these metals, in particular Mn, Fe, Co, Ni or Cu, with at least one alkaline earth metal, for example Mg, Ca, Sr and/or Ba, are also suitable for the purposes of the invention.

The present invention therefore preferably provides the mixture of the invention in which the metal oxide used is an oxide of a metal selected from the group consisting of Mn, Fe, Co, Ni, Cu, combinations thereof and mixed oxides of these metals with at least one alkaline earth metal, for example Mg, Ca, Sr and/or Ba.

In a particularly preferred embodiment, the present invention provides the mixture of the invention in which the metal oxide or semimetal oxide particles are magnetic.

Very particularly preferably preferred metal oxides are iron oxides, for example $Fe_2O_3$, magnetic iron oxides, for example magnetite, maghemite, hematite, cubic ferrites of the general formula (III)

$$M^{2+}{}_x Fe^{2+}{}_{1-x} Fe^{3+}{}_2 O_4 \quad \text{(III)}$$

where
M is selected from among Co, Ni, Mn, Zn and mixtures thereof and
x is ≤1,
hexagonal ferrites, for example calcium, barium or strontium ferrite $MFe_6O_{19}$ where M=Ca, Sr, Ba, and combinations thereof.

In a preferred embodiment, the metal oxide used according to the invention is a magnetic iron oxide selected from the abovementioned group. In a very particularly preferred embodiment, the at least one metal oxide used according to the invention is magnetite. Magnetite has the formula $Fe_3O_4$, in particular $Fe^{II}Fe^{III}{}_2O_4$, and is known to those skilled in the art. Magnetite can be prepared by known processes and is commercially available.

The metal oxide particles used according to the invention can optionally comprise dopants, for example further metals in oxidic or elemental form, for example noble metals such as platinum.

The particles which are present according to the invention generally have a particle size of from 50 nm to 500 μm, preferably from 200 nm to 100 μm, particularly preferably from 500 nm to 10 μm.

The particles which are present according to the invention can generally have any shape, for example spherical, cylindrical, acicular or cuboidal.

Surface-modified particles which are obtained by reacting metal oxide or semimetal oxide particles with at least one compound of the general formula (I)

$$R^1{}_n\text{—Si}(OR^2)_{4-n} \quad \text{(I)}$$

where $R^1$, $R^2$ and n have the abovementioned meaning, where it is important for the purposes of the invention that at least one radical $R^2$ in the compound of the general formula (I) or in the group of the general formula (IIa) is $NR^1{}_4{}^+$ or a group of the general formula $1/(p-x^*y)\ M^{p+}X^{x-}{}_y$, with the abovementioned meanings of $R^1$, p, x, y, M and X, are present in the stable mixture of the invention.

Furthermore, the present invention provides a stable mixture comprising surface-modified particles which are obtained by reacting a metal oxide or semimetal oxide particles with at least one compound of the general formula (I)

$$R^1{}_n\text{—Si}(OR^2)_{4-n} \quad \text{(I)}$$

where $R^1$, $R^2$ and n have the abovementioned meanings, where it is important for the purposes of the invention that at least one radical $R^2$ in the compound of the general formula (I) or in the group of the general formula (IIa) is $NR^1{}_4{}^+$ or a group of the general formula $1/(p-x^*y)\ M^{p+}X^{x-}{}_y$, with the abovementioned meanings of $R^1$, p, x, y, M and X.

Preference is given to the radicals $R^1$ each being, independently of one another, linear or branched, optionally functionalized $C_1$-$C_{30}$-alkyl, particularly preferably $C_1$-$C_{20}$-alkyl, very particularly preferably $C_4$-$C_{12}$-alkyl. In a preferred embodiment, $R^1$ is linear or branched, unfunctionalized $C_1$-$C_{30}$-alkyl, particularly preferably $C_1$-$C_{20}$-alkyl, very particularly preferably $C_4$-$C_{12}$-alkyl. Examples of linear or branched $C_4$-$C_{12}$-alkyl radicals are butyl, in particular, n-butyl, isobutyl, tert-butyl, pentyl, in particular n-pentyl, isopentyl, tert-pentyl, hexyl, in particular n-hexyl, isohexyl, tert-hexyl, heptyl, in particular n-heptyl, isoheptyl, tert-heptyl, octyl, in particular n-octyl, isooctyl, tert-octyl, nonyl, in particular n-nonyl, isononyl, tert-nonyl, decyl, in particular n-decyl, isodecyl, tert-decyl, undecyl, in particular n-undecyl, isoundecyl, tert-undecyl, or dodecyl, in particular n-dodecyl, isododecyl, tert-dodecyl.

Further preference is given to the radicals $R^1$ each being, independently of one another, linear or branched, optionally functionalized $C_2$-$C_{30}$-alkenyl, particularly preferably $C_2$-$C_{20}$-alkenyl, very particularly preferably $C_2$-, $C_3$- or $C_4$-$C_{12}$-alkenyl. Examples of alkenyl radicals which are particularly preferred according to the invention are ethenyl (vinyl), propenyl, in particular n-propenyl, isopropenyl, butenyl, in particular n-butenyl, isobutenyl, tert-butenyl, pentenyl, in particular n-pentenyl, isopentenyl, tert-pentenyl, hexenyl, in particular n-hexenyl, isohexenyl, tert-hexenyl, heptenyl, in particular n-heptenyl, isoheptenyl, tert-heptenyl, octenyl, in particular n-octenyl, isooctenyl, tert-octenyl, nonenyl, in particular n-nonenyl, isononenyl, tert-nonenyl, decenyl, in particular n-decenyl, isodecenyl, tert-decenyl, undecenyl, in particular n-undecenyl, isoundecenyl, tert-undecenyl, or dodecenyl, in particular n-dodecenyl, isododecenyl, tert-dodecenyl.

Further preference is given to the radicals $R^1$ each being, independently of one another, linear or branched, optionally functionalized $C_2$-$C_{30}$-alkynyl, particularly preferably $C_2$-$C_{20}$-alkynyl, very particularly preferably $C_2$-, $C_3$- or $C_4$-$C_{12}$-alkynyl. Examples of alkynyl radicals which are particularly preferred according to the invention are ethynyl, propynyl, in particular n-propynyl, isopropynyl, butynyl, in particular n-butynyl, isobutynyl, tert-butynyl, pentynyl, in particular n-pentynyl, isopentynyl, tert-pentynyl, hexynyl, in particular n-hexynyl, isohexynyl, tert-hexynyl, heptynyl, in particular n-heptynyl, isoheptynyl, tert-heptynyl, octynyl, in particular n-octynyl, isooctynyl, tert-octynyl, nonynyl, in particular n-nonynyl, isononynyl, tert-nonynyl, decynyl, in particular n-decynyl, isodecynyl, tert-decynyl, undecynyl, in particular n-undecynyl, isoundecynyl, tert-undecynyl, or dodecynyl, in particular n-dodecynyl, isododecynyl, tert-dodecynyl.

Further preference is given to the radicals $R^1$ each being, independently of one another, optionally functionalized $C_3$-$C_{20}$-cycloalkyl, particularly preferably $C_3$-$C_{12}$-cycloalkyl, very particularly preferably $C_3$-$C_6$-cycloalkyl, for example cyclopropyl, cyclobutyl, cyclopentyl, cyclohexyl.

Further preference is given to the radicals $R^1$ each being, independently of one another, optionally functionalized $C_3$-$C_{20}$-cycloalkenyl, particularly preferably $C_3$-$C_{12}$-cycloalkenyl, very particularly preferably $C_3$-$C_6$-cycloalkenyl, for example cyclopropenyl, cyclobutenyl, cyclopentenyl, cyclohexenyl.

Further preference is given to the radicals $R^1$ each being, independently of one another, optionally functionalized $C_1$-$C_{20}$-heteroalkyl, particularly preferably $C_1$-$C_{12}$-heteroalkyl. The heteroalkyl radicals present according to the invention are derived from the abovementioned alkyl radicals, with at least one carbon atom being replaced by a heteroatom selected from among N, O, P and S.

Further preference is given to the radicals $R^1$ each being, independently of one another, optionally functionalized $C_5$-$C_{22}$-aryl, particularly preferably $C_5$-$C_{12}$-aryl. Examples of aryl radicals which are preferred according to the invention are phenyl, naphthyl or biaryls.

Further preference is given to the radicals $R^1$ each being, independently of one another, optionally functionalized $C_6$-$C_{23}$-alkylaryl, particularly preferably $C_6$-$C_{13}$-alkylaryl. An example of an alklaryl radical which is preferred according to the invention is benzyl.

Further preference is given to the radicals $R^1$ each being, independently of one another, optionally functionalized $C_6$-$C_{23}$-arylalkyl, particularly preferably $C_6$-$C_{13}$-arylalkyl. Examples of arylalkyl radicals which are preferred according to the invention are tolyl, xylyl, propylbenzyl, hexylbenzyl.

Further preference is given to the radicals $R^1$ each being, independently of one another, optionally functionalized $C_5$-$C_{22}$-heteroaryl, particularly preferably $C_5$-$C_{12}$-heteroaryl.

The abovementioned radicals $R^1$ can optionally be functionalized. Suitable functional groups are, for example, selected from among amino, amido, imido, hydroxyl, ether, aldehyde, keto, carboxylic acid, thiol, thioether, hydroxamate and carbamate groups. The abovementioned radicals $R^1$ can be singly or multiply functionalized. In the case of multiple functionalization, one functional group can be present a plurality of times or various functional groups are simultaneously present. The radicals mentioned for $R^1$ can also be monosubstituted or polysubstituted by the abovementioned alkyl, alkenyl, alkynyl, aryl, alkylaryl, arylalkyl, heteroalkyl or heteroaryl radicals.

Very particularly preferred radicals $R^1$ are octyl, in particular n-octyl, hexyl, in particular n-hexyl and/or butyl, in particular n-butyl, decyl, in particular n-decyl, or dodecyl, in particular n-dodecyl.

For the purposes of the present invention, "independently of one another" means that if a plurality of radicals $R^1$ are present in the compound of the general formula (I) or the group of the general formula (IIa), these can be identical or different.

Preference is given to the radicals $R^2$ each being, independently of one another, hydrogen, linear or branched, optionally functionalized $C_1$-$C_{30}$-alkyl, particularly preferably $C_1$-$C_{20}$-alkyl, very particularly preferably $C_1$-$C_{12}$-alkyl. In a preferred embodiment, $R^2$ is linear or branched, unfunctionalized $C_1$-$C_{30}$-alkyl, particularly preferably $C_1$-$C_{20}$-alkyl, very particularly preferably $C_1$-$C_{12}$-alkyl. Examples of linear or branched $C_1$-$C_{12}$-alkyl radicals are methyl, ethyl, propyl, in particular n-propyl, isopropyl, butyl, in particular n-butyl, isobutyl, tert-butyl, pentyl, in particular n-pentyl, isopentyl, tert-pentyl, hexyl, in particular n-hexyl, isohexyl, tert-hexyl, heptyl, in particular n-heptyl, isoheptyl, tert-heptyl, octyl, in particular n-octyl, isooctyl, tert-octyl, nonyl, in particular n-nonyl, isononyl, tert-nonyl, decyl, in particular n-decyl, isodecyl, tert-decyl, undecyl, in particular n-undecyl, isoundecyl, tert-undecyl, or dodecyl, in particular n-dodecyl, isododecyl, tert-dodecyl.

Further preference is given to the radicals $R^2$ each being, independently of one another, linear or branched, optionally functionalized $C_2$-$C_{30}$-alkenyl, particularly preferably $C_2$-$C_{20}$-alkenyl, very particularly preferably $C_2$-$C_{12}$-alkenyl. Examples of alkynyl radicals which are particularly preferred according to the invention are ethenyl (vinyl), propenyl, in particular n-propenyl, isopropenyl, butenyl, in particular n-butenyl, isobutenyl, tert-butenyl, pentenyl, in particular n-pentenyl, isopentenyl, tert-pentenyl, hexenyl, in particular n-hexenyl, isohexenyl, tert-hexenyl, heptenyl, in particular n-heptenyl, isoheptenyl, tert-heptenyl, octenyl, in particular n-octenyl, isooctenyl, tert-octenyl, nonenyl, in particular n-nonenyl, isononenyl, tert-nonenyl, decenyl, in particular n-decenyl, isodecenyl, tert-decenyl, undecenyl, in particular n-undecenyl, isoundecenyl, tert-undecenyl, or dodecenyl, in particular n-dodecenyl, isododecenyl, tert-dodecenyl.

Further preference is given to the radicals $R^2$ each being, independently of one another, linear or branched, optionally functionalized $C_2$-$C_{30}$-alkynyl, particularly preferably $C_2$-$C_{20}$-alkynyl, very particularly preferably $C_2$-$C_{12}$-alkynyl. Examples of alkynyl radicals which are particularly preferred according to the invention are ethynyl, propynyl, in particular n-propynyl, isopropynyl, butynyl, in particular n-butynyl, isobutynyl, tert-butynyl, pentynyl, in particular n-pentynyl, isopentynyl, tert-pentynyl, hexynyl, in particular n-hexynyl, isohexynyl, tert-hexynyl, heptynyl, in particular n-heptynyl, isoheptynyl, tert-heptynyl, octynyl, in particular n-octynyl, isooctynyl, tert-octynyl, nonynyl, in particular n-nonynyl, isononynyl, tert-nonynyl, decynyl, in particular n-decynyl, isodecynyl, tert-decynyl, undecynyl, in particular n-undecynyl, isoundecynyl, tert-undecynyl, or dodecynyl, in particular n-dodecynyl, isododecynyl, tert-dodecynyl.

Further preference is given to the radicals $R^2$ each being, independently of one another, optionally functionalized $C_3$-$C_{20}$-cycloalkyl, particularly preferably $C_3$-$C_{12}$-cycloalkyl, particularly preferably $C_3$-$C_6$-cycloalkyl, for example cyclopropyl, cyclobutyl, cyclopentyl, cyclohexyl.

Further preference is given to the radicals $R^2$ each being, independently of one another, optionally functionalized $C_3$-$C_{20}$-cycloalkenyl, particularly preferably $C_3$-$C_{12}$-cycloalkenyl, very particularly preferably $C_3$-$C_6$-cycloalkenyl, for example cyclopropenyl, cyclobutenyl, cyclopentenyl, cyclohexenyl.

Further preference is given to the radicals $R^2$ each being, independently of one another, optionally functionalized $C_1$-$C_{20}$-heteroalkyl, particularly preferably $C_4$-$C_{12}$-heteroalkyl. The heteroalkyl radicals which are present according to the invention are derived from the abovementioned alkyl radicals, with at least one carbon atom being replaced by a heteroatom selected from among N, O, P and S.

Further preference is given to the radicals $R^2$ each being, independently of one another, optionally functionalized $C_5$-$C_{22}$-aryl, particularly preferably $C_5$-$C_{12}$-aryl. Examples of aryl radicals which are preferred according to the invention are phenyl, naphthyl or biaryls.

Further preference is given to the radicals $R^2$ each being, independently of one another, optionally functionalized $C_6$-$C_{23}$-alkylaryl, particularly preferably $C_6$-$C_{13}$-alkylaryl. An example of an alkylaryl radical which is preferred according to the invention is benzyl.

Further preference is given to the radicals $R^2$ each being, independently of one another, optionally functionalized $C_6$-$C_{23}$-arylalkyl, particularly preferably $C_6$-$C_{13}$-arylalkyl. Examples of arylalkyl radicals which are preferred according to the invention are tolyl, xylyl, propylbenzyl, hexylbenzyl.

Further preference is given to the radicals $R^2$ each being, independently of one another, optionally functionalized $C_5$-$C_{22}$-heteroaryl, particularly preferably $C_5$-$C_{12}$-heteroaryl.

The abovementioned radicals $R^2$ can optionally be functionalized. Suitable functional groups are, for example, selected from among amino, amido, imido, hydroxy, ether, aldehyde, keto, carboxylic acid, thiol, thioether, hydroxamate and carbamate groups. The abovementioned radicals $R^1$ can be singly or multiply functionalized. In the case of multiple functionalization, one functional group can be present a plurality of times or various functional groups are simultaneously present. The radicals mentioned for $R^2$ can also be monosubstituted or polysubstituted by the abovementioned alkyl, alkenyl, alkynyl, aryl, alkylaryl, arylalkyl, heteroalkyl or heteroaryl radicals.

It is important for the purposes of the invention that at least one radical $R^2$ in the compound of the general formula (I) or in the group of the general formula (IIa) is $NR^1_4{}^+$ or a group of the general formula $1/(p-x*y)\ M^{p+}X^{x-}{}_y$ with the abovementioned meanings of $R^1$, p, x, y, M and X.

In one embodiment, at least one radical $R^2$ is $NR^1_4{}^+$. In this case, the radicals $R^1$ can, independently of one another, have the abovementioned meanings, with particular preference being given in this case to $R^1$ being hydrogen, methyl, ethyl, propyl, in particular n-propyl, octyl, in particular n-octyl, hexyl, in particular n-hexyl, and/or butyl, in particular n-butyl, decyl, in particular n-decyl, or dodecyl, in particular n-dodecyl.

In a further preferred embodiment, at least one radical $R^2$ is a group of the general formula $1/(p-x*y)\ M^{p+}X^{x-}{}_y$, where M is a metal atom selected from the group consisting of metals of the main and transition groups of the Periodic Table of the Elements, X is an anion, p is the oxidation number of the metal atom M, x is 1, 2 or 3 and y is 0, 1 or 2.

X in the abovementioned general formula is generally an anion, for example an anion selected from the group consisting of $Cl^-$, $NO_3{}^-$, $SO_4{}^{2-}$ or $PO_4{}^{3-}$. In these preferred embodiments, x is 1, 2 or 3 and thus corresponds to the negative formal charge on the anions.

The number of anions present in the abovementioned group is described by y. y is therefore particularly preferably 0, 1 or 2, i.e. it is possible for no, one or two further anion(s) to be present in the abovementioned group.

In a preferred embodiment, p is 1, 2, 3, 4, 5, 6 or 7, with particular preference being given to p being 1, 2 or 3.

Since at least one radical $R^2$ in the compound of the general formula (I), optionally comprising at least one group of the general formula (IIa), is $NR^1_4{}^+$ or a group of the general formula $1/(p-x*y)\ M^{p+}X^{x-}{}_y$, this means that, according to the invention, a salt is used as compound of the general formula (I). The positive formal charge(s) on the ammonium cation $NR^1_4{}^+$ or the group $1/(p-x*y)\ M^{p+}X^{x-}{}_y$, is/are, in this embodiment, compensated by the negative formal charge on the oxygen atom. Compounds of the general formula (I) in which at least one radical $R^2$ is $NR^1_4{}^+$ or a group of the general formula $1/(p-x*y)\ M^{p+}X^{x-}{}_y$ which are used according to the invention are uncharged in a particularly preferred embodiment.

The factor $1/(p-x*y)$ is important for the purposes of the invention since the molar amount of metal is dependent on the valence of the metal present and the number and valence of any anions present. For example, if metal atoms present in the oxidation state +3, i.e. p is equal to 3, are used, the molar amount of compound of the general formula (I) is, in the absence of further anions X, three times the molar amount of metal in order to obtain an uncharged Si-comprising salt. If, for example, metal atoms which are present in the oxidation state +2, i.e. p is equal to 2, are used, the molar amount of compound of the general formula (I) is, in the absence of further anions X, twice the molar amount of metal in order to obtain an uncharged Si-comprising salt. If, for example, metal atoms which are present in the oxidation state +1, i.e. p is equal to 1, are used, the molar amount of compound of the general formula (I) is, in the absence of further anions X, equal to the molar amount of metal in order to obtain an uncharged Si-comprising salt. In the case of mixtures of metal atoms having different valences or when particular amounts of anions having particular charges are present, the ratio is calculated correspondingly.

According to the invention, a number of embodiments are possible:

If a monovalent cation such as $Na^+$, $K^+$, etc., is used as cation $M^{p+}$, such a cation is present in each group of the general formula $1/(p-x*y)\ M^{p+}X^{x-}{}_y$.

If a divalent cation such as $Ca^{2+}$, etc., is used as cation $M^{p+}$, the factor $1/(p-x*y)$ has, in the absence of further anions, i.e. y is equal to zero, the value 0.5, i.e. 0.5 equivalents of $Ca^{2+}$ are mathematically present per group $R^2$. According to the invention, this can be realized either by two negatively charged oxygen atoms whose two negative charges are neutralized by a $Ca^{2+}$ cation being present in a compound of the general formula (I) or (IIa), so that each oxygen anion is neutralized mathematically by 0.5 $Ca^{2+}$. It is also possible according to the invention for one negatively charged oxygen atom to be present in each of two compounds of the general formula (I) or (IIa), whose two negative charges in total are neutralized by a $Ca^{2+}$ cation, so that each oxygen anion is mathematically neutralized by 0.5 $Ca^{2+}$. Mixed forms of these embodiments are also possible according to the invention.

In the case of polyvalent cations or mixtures of various cations, optionally with different oxidation numbers, analogous considerations apply.

In general, M is selected from among metals of the main and transition groups of the Periodic Table of the Elements, preferably from groups 1, 2 and 13 (IUPAC nomenclature). M is preferably selected from the group of the alkali metals, for example Li, Na, K, Rb, Cs, Fr, preferably $Li^+$, $Na^+$, $K^+$, $Rb^+$, $Cs^+$, $Fr^+$, where p is in each case equal to 1, from the group of the alkaline earth metals, for example Be, Mg, Ca, Sr, Ba, Ra, preferably $Be^{2+}$, $Mg^{2+}$, $Ca^{2+}$, $Sr^{2+}$, $Ba^{2+}$, $Ra^{2+}$, where p is in each case equal to 2, and/or from group 13 of the Periodic Table of the Elements, for example B, Al, Ga, In, Tl, preferably $B^{3+}$, $Al^{3+}$, $Ga^{3+}$, $In^{3+}$, $Tl^{3+}$, where p is in each case equal to 3.

The present invention therefore preferably provides the mixture of the invention in which $M^{p+}$ is selected from group 1, 2 or 13 of the Periodic Table of the Elements (IUPAC nomenclature).

In a particularly preferred embodiment, at least one radical $R^2$ in the compound of the general formula (I) or in the group of the general formula (IIa) is independently a group of the general formula $1/(p-x*y)\ M^{p+}X^{x-}{}_y$ where p is 1, y is 0 and M is Na and/or K.

The present invention therefore preferably provides the mixture of the invention in which at least one radical $R^2$ in the compound of the general formula (I) or in the group of the general formula (IIa) is independently a group of the general formula $1/(p-x*y)\ M^{p+}X^{x-}{}_y$ where p is 1, y is 0 and M is Na and/or K.

In a further preferred embodiment, $R^2$ is a group of the general formula (IIa)

$$\text{—SiR}^1{}_m(OR^2)_{3-m} \quad \quad \quad \text{(IIa)}$$

where $R^1$ and $R^2$ have, independently of one another, the abovementioned meanings and the indices m can, independently of one another, each be 0, 1, 2 or 3, preferably 1 or 2. The bonding of this group of the general formula (IIa) to the compound of the general formula (I) is via the free bond on the Si atom.

In a particularly preferred embodiment, the radicals $R^1$ in the group of the general formula (IIa) are each, independently of one another, hydrogen, methyl, ethyl, octyl, in particular n-octyl, hexyl, in particular n-hexyl, and/or butyl, in particular n-butyl, decyl, in particular n-decyl, or dodecyl, in particular n-dodecyl.

In a particularly preferred embodiment, the radicals $R^2$ in the group of the general formula (IIa) are each, independently of one another, methyl or ethyl.

In a particularly preferred embodiment, at least one radical $R^2$ in the group of the general formula (IIa) is independently a group of the general formula $1/(p-x*y)\, M^{p+}X^{x-}{}_y$, where p is 1, y is 0 and M is Na and/or K.

The present invention therefore preferably provides the mixture of the invention in which at least one radical $R^2$ in the group of the general formula (IIa) is independently a group of the general formula $1/(p-x*y)\, M^{p+}X^{x-}{}_y$ where p is 1, y is 0 and M is Na and/or K.

If groups of the general formula (IIa) are repeatedly present in the compound of the general formula (I), polysiloxanes are used according to the invention as compounds of the general formula (I). If polysiloxanes comprising groups of the general formula (IIa) are used for the purposes of the invention, these can be linear or branched. Polysiloxanes comprising groups of the general formula (IIa) which are used according to the invention generally have a molecular weight of from 250 to 200 000 g/mol, preferably from 250 to 20 000 g/mol, particularly preferably from 300 to 5000 g/mol.

For the purposes of the present invention, "independently of one another" means that if a plurality of radicals $R^2$ are present in the compound of the general formula (I) or (IIa), these can be identical or different.

In the compound of the general formula (I), n is generally 1, 2 or 3. n in the compound of the general formula (I) is preferably 1 or 2. n in the compound of the general formula (I) is particularly preferably 1.

The present invention therefore preferably provides the mixture of the invention in which n in the compound of the general formula (I) is 1 or 2, particularly preferably 1.

In the polysiloxanes of the general formula (I) comprising groups of the general formula (IIa) the indices m are generally each independently 0, 1, 2 or 3, preferably 1 or 2.

Compounds of the general formula (I) which are particularly preferred according to the invention are selected from the group of salts consisting of
$R^1{}_n$—Si(OR$^2$)$_{4-n}$ where $R^1$ is methyl, ethyl, butyl, pentyl, hexyl, octyl, decyl and/or dodecyl, $R^2$ is Na, K and/or NH$_4$ and n is 1, 2 or 3,
or
$R^1{}_n$—Si(OR$^2$)$_{4-n}$ where $R^1$ is methyl, ethyl, butyl, pentyl, hexyl, octyl, decyl and/or dodecyl, $R^2$ is 0.5 Ca and/or 0.5 Mg and n is 1, 2 or 3, with what has been said above applying in respect of the divalent cations. In these particularly preferred embodiments, no further anions $X^{x-}$ are present, i.e. y in the formula $1/(p-x*y)$ is equal to zero.

Very particularly preferred compounds of the general formula (I) are selected from the group consisting of (NaO)(CH$_3$)Si(OH)$_2$, (NaO)(C$_2$H$_5$)Si(OH)$_2$, (NaO)(C$_5$H$_{11}$)Si(OH)$_2$, (NaO)(C$_8$H$_{17}$)Si(OH)$_2$, (KO)(CH$_3$)Si(OH)$_2$, (KO)(C$_2$H$_5$)Si(OH)$_2$, (KO)(C$_5$H$_{11}$)Si(OH)$_2$, (KO)(C$_8$H$_{17}$)Si(OH)$_2$, (NH$_4$O)(CH$_3$)Si(OH)$_2$, (NH$_4$O)(C$_2$H$_5$)Si(OH)$_2$, (NH$_4$O)(C$_5$H$_{11}$)Si(OH)$_2$, (NH$_4$O)(C$_8$H$_{17}$)Si(OH)$_2$, (NaO)$_2$(CH$_3$)Si(OH), (NaO)$_2$(C$_2$H$_5$)Si(OH), (NaO)$_2$(C$_5$H$_{11}$)Si(OH), (NaO)$_2$(C$_8$H$_{17}$)Si(OH), (KO)$_2$(CH$_3$)Si(OH), (KO)$_2$(C$_2$H$_5$)Si(OH), (KO)$_2$(C$_5$H$_{11}$)Si(OH), (KO)$_2$(C$_8$H$_{17}$)Si(OH), (NH$_4$O)$_2$(CH$_3$)Si(OH), (NH$_4$O)$_2$(C$_2$H$_5$)Si(OH), (NH$_4$O)$_2$(C$_5$H$_{11}$)Si(OH), (NH$_4$O)$_2$(C$_8$H$_{17}$)Si(OH), (NaO)$_3$(CH$_3$)Si, (NaO)$_3$(C$_2$H$_5$)Si, (NaO)$_3$(C$_5$H$_{11}$)Si, (NaO)$_3$(C$_8$H$_{17}$)Si, (KO)$_3$(CH$_3$)Si, (KO)$_3$(C$_2$H$_5$)Si, (KO)$_3$(C$_5$H$_{11}$)Si, (KO)$_3$(C$_8$H$_{17}$)Si, (NH$_4$O)$_3$(CH$_3$)Si, (NH$_4$O)$_3$(C$_2$H$_5$)Si, (NH$_4$O)$_3$(C$_5$H$_{11}$)Si, (NH$_4$O)$_3$(C$_8$H$_{17}$)Si, (NaO)(CH$_3$)$_2$Si(OH), (NaO)(C$_2$H$_5$)$_2$Si(OH), (KO)(CH$_3$)$_2$Si(OH), (KO)(C$_2$H$_5$)$_2$Si(OH), (NaO)$_2$(CH$_3$)$_2$Si, (NaO)$_2$(C$_2$H$_5$)$_2$Si, (KO)$_2$(CH$_3$)$_2$Si, (KO)$_2$(C$_2$H$_5$)$_2$Si, Ca$^+$[(O$^-$)(CH$_3$)Si(OH)$_2$]$_2$, Ca$^+$[(O$^-$)(C$_2$H$_5$)Si(OH)$_2$]$_2$, Ca$^+$[(O$^-$)(C$_5$H$_{11}$)Si(OH)$_2$]$_2$, Ca$^+$[(O$^-$)(C$_8$H$_{17}$)Si(OH)$_2$]$_2$, Ca$^+$[(O$^-$)(CH$_3$)$_2$Si(OH)]$_2$, Ca$^+$[(O$^-$)(C$_2$H$_5$)$_2$Si(OH)]$_2$, Ca$^+$[(O$^-$)$_2$(CH$_3$)Si(OH)], Ca$^+$[(O$^-$)$_2$(C$_2$H$_5$)Si(OH)], Ca$^+$[(O$^-$)$_2$(C$_5$H$_{11}$)Si(OH)], Ca$^+$[(O$^-$)$_2$(C$_8$H$_{17}$)Si(OH)], Ca$^+$[(O$^-$)$_2$(CH$_3$)$_2$Si], Ca$^+$[(O$^-$)$_2$(C$_2$H$_5$)$_2$Si].

A class of polysiliconates of the general formula (I) comprising groups of the general formula (IIa) which is preferred for the purposes of the invention is that of polymethylsiliconates and polydimethylsiliconates having sodium, potassium, magnesium, calcium or ammonium as cation.

The present invention also provides a process for producing a surface-modified particle as defined above by bringing the metal oxide or semimetal oxide particle to be modified and a compound of the general formula (I) as defined above into contact with one another.

The reaction of the abovementioned metal oxide or semimetal oxide particles with the compounds of the general formula (I) or the polysiloxanes of the general formula (I) comprising groups of the general formula (IIa) can be carried out by processes known to those skilled in the art, for example by contacting of the substrates in a solvent, for example toluene or water, at a temperature in the range from room temperature to the boiling point of the solvent. In addition, the substrates may be contacted with further reactants or reaction accelerators, for example acids, $CO_2$, etc., in the same step or a separate step. After conventional work-up, the reaction product of metal oxide or semimetal oxide particles and compounds of the general formula (I) or polysiloxanes of the general formula (I) comprising groups of the general formula (IIa) can be obtained.

The silicon compounds are preferably fixed to the metal oxide or semimetal oxide surface by condensation of the surface hydroxyl groups of the oxide M-OH with silanol groups of the silicon compound (Si—OH+M-OH→Si—O-M+H$_2$O). The silanol groups can be originally comprised in the starting silicon compound of the formula (I) or a subunit (IIa) or be formed in situ. This can be effected, for example, by hydrolysis of the silicon ether (Si—OR+H$_2$O) to the silanol (Si—OH+ROH). SiOR$^2$ can be hydrolyzed, R' and all further radicals mentioned cannot be hydrolyzed.

The process of the invention can, for example, be carried out by spraying a reagent solution comprising the compound of the general formula (I) onto the metal oxide or semimetal oxide particles. A further method of bringing the metal oxide or semimetal oxide particles to be modified and a compound of the general formula (I) as defined above into contact with one another comprises, for example, suspending the metal oxide or semimetal oxide particles in a compound of the general formula (I) or in a solution of a compound of the general formula (I) in a suitable solvent. Corresponding processes are known per se to those skilled in the art.

After the compound of the formula (I) has been brought into contact with the metal oxide or semimetal oxide particles, a further treatment step may be necessary in order to complete the fixing reaction. This can be carried out, for example, by adjusting the pH, heat treatment, treatment with various gas atmospheres, e.g. $CO_2$ or $SO_2$, or a combination of such steps.

The stable mixture of the invention comprises at least one solvent, at least one surface-active substance or a mixture thereof in addition to the abovementioned functionalized metal oxide or semimetal oxide particles.

It has surprisingly been found that the reaction products according to the invention, i.e. the surface-functionalized metal oxide or semimetal oxide particles, are particularly stable in mixtures with solvents and/or surface-active compounds, i.e. no detachment of the silicon compounds bound to the surface occurs.

The at least one solvent present in the mixture of the invention is preferably selected from the group consisting of aromatic hydrocarbons, for example benzene, toluene, xylene, alcohols, for example methanol, ethanol, propanols such as n-propanol, isopropanol, butanols such as n-butanol, isobutanol, tert-butanol, ethers such as diethyl ether, methyl tert-butyl ether, isobutyl tert-butyl ether, cyclic ethers such as tetrahydrofuran, dioxane, esters, cyclic esters, alkanes such as hexane, cycloalkanes such as cyclohexane, olefins, cycloolefins, water and mixtures thereof. If mixtures of solvents are used according to the invention, preference is given to using solvents which are completely miscible with one another, i.e. form a single phase on mixing.

The present invention therefore preferably provides the mixture of the invention in which the at least one solvent is selected from the group consisting of aromatic hydrocarbons, preferably benzene, toluene, xylene, alcohols, for example methanol, ethanol, propanols such as n-propanol, isopropanol, butanols such as n-butanol, isobutanol, tert-butanol, ethers such as diethyl ether, methyl tert-butyl ether, isobutyl-tert-butyl ether, cyclic ethers such as tetrahydrofuran, dioxane, esters, cyclic esters, alkanes such as hexane, cycloalkanes such as cyclohexane, olefins, cycloolefins, water and mixtures thereof.

In a preferred embodiment, the mixture of the invention is used in processes in which the surface-modified particles are brought into contact with particularly large amounts of solvents.

The mixture of the invention generally has a solids content of up to 70% by weight, preferably up to 60% by weight. The content of at least one solvent in the mixture of the invention is therefore generally at least 30% by weight, preferably at least 40% by weight, i.e. in general from 30 to 99.9% by weight, preferably from 40 to 99.9% by weight, of solvent. According to the invention, the solids content is the content of particles which have been modified on the surface according to the invention and any further solids present.

The at least one surface-active substance present in the mixture of the invention is preferably selected from the group consisting of nonionic, anionic, cationic or zwitterionic surfactants and mixtures thereof.

Preferred examples of nonionic surfactants are fatty alcohol polyglycol ethers, in particular fatty alcohol polyethylene glycol ethers.

Preferred examples of anionic surfactants are alkylbenzenesulfonates, secondary alkanesulfonates, α-olefinsulfonates, fatty alcohol sulfates or fatty alcohol ether sulfates.

Preferred examples of cationic surfactants are stearyltrimethylammonium salts.

Preferred examples of zwitterionic surfactants are sultaines, fatty acid amidoalkylhydroxysultaine or alkyl betaines.

Particularly preferred surface-active substances are sodium alkylphenol ether sulfates.

The at least one surface-active substance is generally present in the mixture of the invention in an amount of from 0.001 to 20% by weight, preferably from 0.01 to 15% by weight, particularly preferably from 0.1 to 10% by weight, in each case based on the total mixture. If at least one surface-active substance is present according to the invention, the abovementioned amount of at least one solvent is modified accordingly.

The surface-functionalized metal oxide or semimetal oxide particles are generally present in the mixture of the invention in an amount of from 0.1 to 70% by weight, preferably from 0.1 to 60% by weight.

If further solids are optionally present in the mixture of the invention, the abovementioned amount of surface-functionalized metal oxide or semimetal oxide particles is modified accordingly.

In all possible embodiments, the amounts of surface-functionalized metal oxide or semimetal oxide particles, at least one solvent, optionally present surface-active substances and optionally present further solids add up to 100% by weight.

Apart from the functionalized particles, the at least one solvent and/or the at least one surface-active substance, the mixture of the invention can comprise further components, for example oxidic or metallic solids and further hydrophobic components. The sum of the amounts of the components present in the mixture of the invention in each case add up to 100% by weight.

The mass ratio of solvent to modified particles in the mixture of the invention is generally greater than 500, preferably 1000, particularly preferably greater than 5000, very particularly preferably greater than 10 000.

For the purposes of the present invention, the term "stable mixture" means that the surface-functionalized metal oxide or semimetal oxide particles present in the mixture of the invention are not changed in the mixture, i.e. the silyl groups present on the surface are not detached from the surface of the metal oxide or semimetal oxide particles, for example by hydrolysis, so that the mixture of the invention as a whole does not change or changes only slightly. That a mixture comprising surface-modified particles is stable for the purposes of the present invention can be demonstrated, for example, by the fact that such particles which are in contact with solvents and/or surface-active substance in a mixture according to the invention remain chemically and/or physically unchanged. This can, for example, be determined by elemental analysis or determination of the hydrophobic properties, for example by determination of the ability to float or the contact angle.

The present invention also provides a process for treating surface-modified particles according to the invention with at least one solvent, wherein the mass ratio of solvent to modified particle is greater than 500.

As regards the surface-modified particles and the solvents, what has been said above in respect of the mixture according to the invention applies to the process of the invention.

In the process of the invention, the mass ratio of surface-modified particle and the at least one solvent is generally greater than 500, preferably greater than 1000, particularly preferably greater than 5000, very particularly preferably greater than 10 000.

In this process of the invention, the surface-modified particles according to the invention are brought into contact, i.e. treated, with a relatively large amount of solvent. Corresponding systems according to the invention in which this treatment can be carried out are, for example, flowing systems in which the surface-modified particles of the invention are brought into contact in, for example, continuous processes with further substances, particles, materials, etc., for example continuous processes for agglomeration with further substances, particles, materials, etc., in solution or dispersion. The process of the invention also relates to deagglomeration of agglomerates of the surface-modified particles of the invention and further substances, particles or materials, or of agglomerates of the surface-modified particles with themselves, for example likewise in flowing systems.

The present invention also provides for the use of surface-modified particles according to the invention in systems in which the modified particles are brought into contact with at least one solvent, wherein the mass ratio of solvent to modified particles is greater than 500.

As regards the surface-modified particles and the solvents, what has been said above in respect of the mixture of the invention applies.

The mass ratio of surface-modified particle and the at least one solvent is generally greater than 500, preferably greater than 1000, particularly preferably greater than 5000, very particularly preferably greater than 10 000.

In this use according to the invention, the surface-modified particles of the invention are brought into contact with a relatively large amount of solvent. Corresponding systems according to the invention in which this contacting can be carried out are, for example, flowing systems in which the surface-modified particles of the invention are brought into contact in, for example, continuous processes with further substances, particles, materials, etc., for example continuous processes for agglomeration with further substances, particles, materials, etc., in solution or dispersion. The use according to the invention also relates to deagglomeration of agglomerates of the surface-modified particles of the invention and further substances, particles or materials, or of agglomerates of surface-modified particles with themselves, for example likewise in flowing systems.

The present invention also provides for the use of surface-modified particles according to the invention, in particular magnetic particles, in agglomeration-deagglomeration cycles.

In this use too, what has been said in respect of the mixture of the invention applies to the surface-modified particles and the solvents.

According to the invention, an agglomeration-deagglomeration cycle is a process in which the surface-functionalized particles of the invention, in particular magnetic particles, are brought into contact with themselves or other particles, substances, materials, etc., in solution or dispersion and agglomerate as a result of hydrophobic interaction, ionic forces, van der Waals interactions and/or other attractive forces. These agglomerates are then processed in further processes, for example separated from other components and/or the solution or dispersion. After this treatment, the agglomerates are then separated again, i.e. deagglomerated, so that the surface-functionalized particles and the other particles, substances, materials, etc., are again present separately (deagglomeration). Examples of agglomeration-deagglomeration cycles which are preferred according to the invention are chemical, physical or biological test methods or separation processes, decontamination of contaminated, for example heavy metal-contaminated earth, water purification, recycling of electrical/electronic scrap or gravity separation.

In chemical, physical or biological test methods or separation processes, use is made of, for example, specifically modified magnetic nanoparticles which have anchor groups for a specific antigen or virus, e.g. borrelia, HIV, hepatitis, on their surface. These specific anchor groups correspond, in particular, to the abovementioned group R' which has a structure corresponding to the respective separation or test task, for example as a result of the presence of the abovementioned functional groups. Bonding of these antigens/viruses to the modified particle surface (agglomeration) enables these constituents to be separated off from a solution by means of magnetic separation and thus detected. The functionalized magnetic particles are then recycled by means of surfactants which again release the electrostatic, adhesive or van der Waals interaction between functionalized magnetic particle and antigen/virus (deagglomeration). In this way, the functionalized magnetite particles can be reused.

The modified particles of the invention, in particular magnetic particles, can be used in water purification. Here, for example, it is possible to use functionalized magnetite particles which remove organic constituents, suspended materials or fat droplets from the water by effecting hydrophobic agglomeration between the functionalized magnetite particle and the hydrophobic contaminant. These hydrophobic agglomerates can be separated off by magnetic separation. In order that water purification is economical, it is useful to "unload" the hydrophobic magnetite particles from the contaminant again and return them to the circuit. This "unloading" can once again be effected by deagglomeration using a specific surface-active substance (surfactant) and/or by means of a specific solvent or solvent mixture.

Recycling of electrical/electronic scrap can, for example, be carried out by magnetic recovery of materials of value (Ir, Pt, Ru) from electrical/electronic scrap, once again preferably using modified magnetite particles which, after hydrophobicization of the materials of value to be separated, can agglomerate with these and be separated off. After the agglomerates have been separated off, they are deagglomerated again so that the modified magnetic particles can be reused.

A further example is gravity separation, e.g. by means of cyclones known to those skilled in the art. In this way, relatively dense constituents can be separated off from less dense constituents by means of a gravity separation. If the densities of the individual components differ only slightly, e.g. Pt-doped hematite and undoped hematite, the density of the component to be separated off can be increased by agglomeration with a further component. Here, for example, the Pt-doped hematite component is hydrophobicized according to the invention to give modified particles, so that addition of hydrophobicized barium sulfate gives an agglomerate of the modified hematite and barium sulfate which has a greater density difference from the undoped hematite. After the agglomerate has been separated off, it can be deagglomerated again.

The present invention therefore also preferably provides for the use according to the invention in which the agglomeration-deagglomeration cycle is a chemical, physical or biological test method or separation process, water purification, purification of contaminated, for example heavy metal-polluted earth, recycling of electrical/electronic scrap or gravity separation.

An advantage of the invention is that the particles which have been surface-modified according to the invention are stable under the conditions prevailing in agglomeration and especially deagglomeration and can therefore preferably be reused.

EXAMPLES

Example 1

General Methods

Example 1.1

Preparation of the Alkali Metal Alkylsiliconates Used

The preparation of the alkali metal alkylsiliconates is carried out by the method in R. Murugavel et al., *Solid State*

*Sciences* 2001, 3 (1-2), 169-182. As an alternative, the procedure in the examples in GB675188A can be employed.

For example, $^n$OctSi(ONa)$_3$ is prepared by introducing 1 mol of $^n$OctSi(OMe)$_3$ from ABCR (97% pure) into a solution of 10 mol of NaOH in 400 g of water over a period of 30 minutes. The reaction is then completed under reflux within 4 hours. Distilling off the solvent gives a concentrated solution or complete drying gives the product as a solid.

Example 1.2

Repeated Treatment of the Solid with Surfactant Solution 10 g of solid to be examined are stirred in 1 l of a 0.2% strength by weight solution of Lutensit A-ES from BASF SE (mixture of sodium alkylphenol ether sulfates) in water for 2 hours at room temperature. The solid is subsequently filtered off and washed with 1 l of water, 100 ml of ethanol and 100 ml of acetone. The filter cake is dried at 120° C. under reduced pressure for 4 hours. Samples are subsequently taken for analysis. The remaining product is used for the renewed washing tests.

Example 1.3

Rapid Test for Ability to Float on Water 3 ml of water are placed in a 5 ml test tube. The solid to be examined is subsequently carefully placed on the surface of the water by means of a spatula. The solid in the test tube is subsequently observed to see whether the solid sinks or remains afloat. In the case of floating solids, the closed vessel is shaken for 10 s. The solid in the test tube is subsequently observed to see whether the solid floats again or remains under water.

Example 1.4

Contact Angle Measurement

Contact Angle Measurement on Powders:

Contact angles are measured using a standard instrument (Dropshape Analysis Instrument, Kruss DAS 10). A silhouette of the drop is recorded by means of a CCD camera and the drop shape is determined by computer-aided image analysis. The measurements are, unless indicated otherwise, carried out as described in DIN 5560-2.

a) Production of a Homogeneous Powder Layer

The magnetite powder is applied as an appropriately 1 mm thick layer onto a 100 µm thick BASF Acronal V215 adhesive dispersion on a PET film. Using a spatula, the powder is pressed into the adhesive and excess material which does not adhere is removed by shaking. Finally, remaining loose material is removed by blowing purified nitrogen under pressure over the specimen. This method gives a clean, homogeneous powder surface over the total area of the substrate of 75 mm×25 mm.

Powder surfaces normally display a certain roughness and contact angle or the measurement thereof are sensitive to this roughness. A direct comparison of the hydrophobicity can therefore be carried out only on powders having the same particle size distribution and particle shape. Careful surfaces analyses using ToF-SIMS have shown that the surface of the powder layer produced by this method has no traces of adhesive and is representative of the powder.

b) Dynamic, Progressive Contact Angle Measurement

One milliliter of water is placed as a drop on the surface and 2 µl/min of water are continuously added. 20 µl of liquid volume are added continuously in this way. Starting from a minimal volume of about 3 µl, contact angles are measured while the needle of the syringe used for introduction remains in the drop. Contour measurements are carried out at a rate of about 0.5 Hz and are evaluated by means of a tangent method in order to determine the contact angle directly at the three-phase contact line. These contact angles are averaged over time, and five progressive drops are measured at various positions for each sample and the average value together with a standard deviation is determined.

Example 1.5

Recycling Experiments

An experiment is carried out on the use of magnetite hydrophobicized according to the respective example as reusable carrier for the decontamination of (heavy metal-) contaminated earth. For this purpose, 3 g of magnetite were dispersed in a system comprising 100 g of a sand mixture (solids content: 1% by weight). This sand mixture comprises 99% by weight of inorganic siliceous constituents (e.g. feltspars, mica, iron pyrites) and 1% by weight of a specific hydrophobicized inorganic As-comprising contaminant (Enargite). Hydrophobicization of this inorganic contaminant is carried out using butylxanthate. After vigorous mixing of the hydrophobicized magnetite with this sand mixture, the arsenic component is separated off by means of hydrophobic flocculation with the magnetite. The hydrophobic constituents are collected and treated with a 0.1% strength by weight solution of a surfactant (Lutensit A-ES from BASF SE). In a subsequent magnetic separation step, the magnetic constituents are separated from the nonmagnetic As-comprising impurities. The hydrophobic magnetite is washed with a 1:1 mixture of water and EtOH, filtered off and remixed with a freshly produced sand mixture. The process is repeated a total of ten times.

Example 2

Production of Hydrophobicized Magnetite

Example 2.1

Magnetic Pigment 345 from BASF SE Silanized with $^n$OctSi(OK)$_3$ (According to the Invention)

Synthesis: 10 g of magnet pigment 345 (magnetite Fe$^{II}$(Fe$^{III}$)$_2$O$_4$) from BASF SE are added to a solution of 370 mg of $^n$OctSi(OK)$_3$ in 30 ml of water. The solution is stirred for 30 min at room temperature. The product is dried at 40° C. under reduced pressure. Then the product is stored at 40° C. in air for 7 days. The resulting solid is washed with water until the pH of the washing water does not change any more. Then it is dried overnight in air at 40° C. The dried product is, after preliminary comminution, brushed through an analytical sieve (400 µm) and thus deagglomerated and homogenized.

Analysis:

Floatation test: fresh solid and solid which has been washed ten times float equally well on water (also after shaking under);

Contact angle: fresh 146°, washed ten times 139°;

Recycling test: When the yield of the As component is detected, the yield of 92% in the first cycle drops to only 90% in the tenth cycle when using the "OctSi(OK)$_3$-silanized magnetic pigment 345 from BASF SE.

Example 2.2

"BuSi(OH)$_2$(ONa)-Silanized Magnetic Pigment 345 from BASF SE (According to the Invention)

Synthesis: The synthesis is carried out according to the scheme described in example 2.1. However, 350 mg of "BuSi(OH)$_2$(ONa) are used and the product is stored at 120° C. in a CO$_2$ atmosphere.

Analysis:

Floatation test: fresh solid and solid which has been washed ten times float equally well on water (also after shaking under);

Contact angle: fresh 154°, washed ten times 152°;

Recycling test: When the yield of the As component is detected, the yield of 95% in the first cycle drops to only 91% in the tenth cycle when using the "BuSi(OH)$_2$(ONa)-silanized magnetic pigment 345 from BASF SE.

Example 2.3

Ca$^{2+}$)["Pr(Me)Si(OH)(O$^-$)]$_2$-Silanized Magnetic Pigment 345 from BASF SE (According to the Invention Synthesis: The synthesis is carried out according to the scheme described in example 2.1. However, 340 mg of (Ca$^{2+}$)["Pr(Me)Si(OH)(O$^-$)]$_2$ are used as silanization reagent.

Analysis:

Floatation test: fresh solid and solid which has been washed ten times float equally well on water (also after shaking under);

Contact angle: fresh 142°, washed ten times 136°;

Recycling test: When the yield of the As component is detected, the yield of 89% in the first cycle drops to only 87% in the tenth cycle when using the (Ca$^{2+}$)["Pr(Me)Si(OH)(O$^-$)]$_2$-silanized magnetic pigment 345 from BASF SE.

Example 3

Comparative Examples

Comparative Example 3.1

Commercial, Hydrophobic Magnetite Bayoxide E8707 H from Lanxess (not According to the Invention)

Analysis:

Floatation test: fresh solid floats on water even after shaking under, while solid which has been washed twice no longer floats;

Contact angle: fresh 158°, washed ten times 116°

Recycling: Comparative tests using a previously hydrophobicized magnetite from Lanxess (product: Bayoxide E8707 H) display a dramatic loss in yield of over 40% after only the fourth cycle. The experiments using this product are then stopped.

Comparative Example 3.2

"OctMe$_2$SiCl-Silanized Magnetic Pigment 345 from BASF SE (not According to the Invention)

Synthesis: Under a protective atmosphere, 10 g of magnetic pigment 345 from BASF SE are suspended in 20 ml of toluene. The suspension is heated to 70° C., and 0.3 g of "OctMe$_2$SiCl (97% strength, from ABCR) are then added. The reaction mixture is subsequently maintained at 70° C. for 4 hours while stirring. The solid is subsequently filtered off, washed firstly with 50 ml of toluene, then 50 ml of methanol and finally water until the washings are free of chloride. The product is dried at 120° C. under reduced pressure for 4 hours. The dried product is, after preliminary comminution, brushed through an analytical sieve (400 μm) and thus deagglomerated and homogenized.

Analysis:

Floatation test: solid floats on water (even after shaking under), while solid washed once no longer floats on water;

Contact angle: fresh 148°, washed once 120°, washed ten times 98°

Comparative Example 3.3

"BuMe$_2$SiCl-Silanized Magnetic Pigment 345 from BASF SE (not According to the Invention)

Synthesis: The synthesis is carried out according to the scheme described in example 2.1. However, 0.3 g of "BuMe$_2$SiCl (97% strength from ABCR) is used as silanization reagent.

Analysis:

Floatation test: solid floats on water (not after shaking under), while solid washed once no longer floats on water;

Contact angle: fresh 103°, washed ten times 89°

Comparative Example 3.4

Magnetic Pigment 345 from BASF SE Hydrophobicized with Octylphosphonic Acid (not According to the Invention)

Synthesis: 8.0 kg of water are placed in an apparatus comprising a 12 l plastic bucket with spout as stirred vessel and a metal stirrer. 2 kg of magnetic pigment 345 from BASF SE are subsequently introduced and the stirring speed of the metal stirrer is selected so that the pigment does not sediment and air is also not drawn in (no head of foam is formed). 12.5 g of n-octylphosphonic acid (OPA, 80% strength) from Albright & Wilson are subsequently added all at once and all the starting materials are mixed in air at room temperature for 1.5 hours. After the end of the stirring time, the suspension is poured on to a porcelain filter (d=24 cm with an MN 85/90 paper filter from Macherey-Nagel). Cracks formed in the filter cake are wiped shut to improve the washing action. The solid is dried overnight at 110° C. in a convection drying oven. The dried product is, after preliminary comminution, brushed through an analytical sieve (400 μm) and thus deagglomerated and homogenized.

Analysis:

Elemental analysis: 0.06% of P in the end product;

Recycling test: Even after the third cycle, only an unsatisfactory yield of the As-comprising impurity of less than 50% is detected. The experiments are subsequently stopped.

The invention claimed is:

1. A stable mixture, comprising:
a surface-modified particle;
a solvent; and
a surface-active substance or a mixture thereof, wherein the surface modified particle is obtained by a process comprising:
(A) reacting a magnetic iron oxide particle having a particle size from 500 nm to 500 μm with at least one compound of formula (I):

$$R^1{}_n\text{—Si}(OR^2)_{4-n} \qquad (I),$$

wherein:
each $R^1$ is independently hydrogen; a linear or branched, optionally functionalized $C_1$-$C_{30}$-alkyl; a linear or branched, optionally functionalized $C_2$-$C_{30}$-alkenyl; a linear or branched, optionally functionalized $C_2$-$C_{30}$-alkynyl; an optionally functionalized $C_3$-$C_{20}$-cycloalkyl; an optionally functionalized $C_3$-$C_{20}$-cycloalkenyl; an optionally functionalized $C_1$-$C_{20}$-heteroalkyl; an optionally functionalized $C_5$-$C_{22}$-aryl; an optionally functionalized $C_6$-$C_{23}$-alkylaryl; an optionally functionalized $C_6$-$C_{23}$-arylalkyl; and an optionally functionalized $C_5$-$C_{22}$-heteroaryl, each $R^2$ is independently hydrogen; a linear or branched, optionally functionalized $C_1$-$C_{30}$-alkyl; a linear or branched, optionally functionalized $C_2$-$C_{30}$-alkenyl; a linear or branched, optionally functionalized $C_2$-$C_{30}$-alkynyl; an optionally functionalized $C_3$-$C_{20}$-cycloalkyl; an optionally functionalized $C_3$-$C_{20}$-cycloalkenyl; an optionally functionalized $C_1$-$C_{20}$-heteroalkyl; an optionally functionalized $C_5$-$C_{22}$-aryl; an optionally functionalized $C_6$-$C_{23}$-alkylaryl; an optionally functionalized $C_6$-$C_{23}$-arylalkyl; an optionally functionalized $C_5$-$C_{22}$-heteroaryl; $NR^1{}_4{}^+$; a group of formula $1/(p-x*y)\, M^{p+}X^{x-}{}_y$, wherein M is a metal atom selected from the group consisting of a metal of main groups and a metal of transition groups of the Periodic Table of the Elements, X is an anion, p is the oxidation number of M, x is 1, 2 or 3, and y is 0, 1 or 2; a group of formula (IIa)

$$\text{—SiR}^1{}_m(OR^2)_{3-m} \qquad (IIa),$$

wherein:
each m is independently a number of 0, 1, 2 or 3,
n is a number of 1, 2 or 3, and
at least one $R^2$ in the compound of formula (I) or in the group of formula (IIa) is $NR^1{}_4{}^+$ or a group of the general formula $1/(p-x*y)\, M^{p+}X^{x-}{}_y$, wherein the magnetic iron oxide particle comprises at least one selected from the group consisting of: magnetite and cubic ferrites of formula (III)

$$M^{2+}{}_x Fe^{2+}{}_{1-x} Fe^{3+}{}_2 O_4 \qquad (III),$$

wherein:
M is Co, Ni, Mn, Zn or any mixture thereof; and
x is ≤1, and
hexagonal ferrites of formula (IV):

$$MFe_6O_{19} \qquad (IV),$$

wherein M is Ca, Sr, Ba, and combinations thereof.

2. The mixture according to claim 1, wherein M is selected from the group consisting of a metal of Group 1, a metal of Group 2, and a metal of Group 13 of the Periodic Table of the Elements.

3. The mixture according to claim 1, wherein a mass ratio of the solvent to the surface-modified particle is greater than 500.

4. The mixture according to claim 1, wherein, in formula (I), n is 1 or 2.

5. The mixture according to claim 1, wherein at least one $R^2$ in the compound of formula (I) or in the group of formula (IIa) is independently methyl or ethyl.

6. The mixture according to claim 1, wherein at least one $R^2$ in the compound of formula (I) or in the group of formula (IIa) is independently a group of formula $1/(p-x*y)\, M^{p+}X^{x-}{}_y$, wherein
p is 1,
y is 0, and
M is Na or K.

7. The mixture according to claim 1, wherein the solvent is at least one selected from the group consisting of an aromatic hydrocarbon, an alcohol, an ether, an ester, an alkane, a cycloalkane, an olefin, a cycloolefin, and water.

8. The mixture according to claim 1, wherein the surface-active substance is at least one selected from the group consisting of a nonionic surfactant, an anionic surfactant, a cationic surfactant and a zwitterionic surfactant.

9. A process for producing a surface-modified particle, the process comprising:
contacting a magnetic iron oxide particle having a particle size from 500 nm to 500 μm with a compound of formula (I):

$$R^1{}_n\text{—Si}(OR^2)_{4-n} \qquad (I),$$

wherein
each $R^1$ is independently hydrogen; a linear or branched, optionally functionalized $C_1$-$C_{30}$-alkyl; a linear or branched, optionally functionalized $C_2$-$C_{30}$-alkenyl; a linear or branched, optionally functionalized $C_2$-$C_{30}$-alkynyl; an optionally functionalized $C_3$-$C_{20}$-cycloalkyl; an optionally functionalized $C_3$-$C_{20}$-cycloalkenyl; an optionally functionalized $C_1$-$C_{20}$-heteroalkyl; an optionally functionalized $C_5$-$C_{22}$-aryl; an optionally functionalized $C_6$-$C_{23}$-alkylaryl; an optionally functionalized $C_6$-$C_{23}$-arylalkyl; and an optionally functionalized $C_5$-$C_{22}$-heteroaryl, each $R^2$ is independently hydrogen; a linear or branched, optionally functionalized $C_1$-$C_{30}$-alkyl; a linear or branched, optionally functionalized $C_2$-$C_{30}$-alkenyl; a linear or branched, optionally functionalized $C_2$-$C_{30}$-alkynyl; an optionally functionalized $C_3$-$C_{20}$-cycloalkyl; an optionally functionalized $C_3$-$C_{20}$-cycloalkenyl; an optionally functionalized $C_1$-$C_{20}$-heteroalkyl; an optionally functionalized $C_5$-$C_{22}$-aryl; an optionally functionalized $C_6$-$C_{23}$-alkylaryl; an optionally functionalized $C_6$-$C_{23}$-arylalkyl; an optionally functionalized $C_5$-$C_{22}$-heteroaryl; $NR^1{}_4{}^+$; a group of formula $1/(p-x*y)\, M^{p+}X^{x-}{}_y$, wherein M is a metal atom selected from the group consisting of a metal of main groups and a metal of transition groups of the Periodic Table of the Elements, X is an anion, p is the oxidation number of M, x is 1, 2 or 3, and y is 0, 1 or 2; a group of formula (IIa)

$$\text{—SiR}^1{}_m(OR^2)_{3-m} \qquad (IIa),$$

wherein:
each m is independently a number of 0, 1, 2, or 3,
n is a number of 1, 2 or 3, and
at least one $R^2$ in the compound of formula (I) or in the group of formula (IIa) is $NR^1{}_4{}^+$ or a group of the general formula $1/(p-x*y)\, M^{p+}X^{x-}{}_y$, wherein the magnetic iron oxide particle comprises at least one selected from the group consisting of: magnetite and cubic ferrites of formula (III)

$$M^{2+}_x Fe^{2+}_{1-x} Fe^{3+}_2 O_4 \quad (III),$$

wherein:
M is Co, Ni, Mn, Zn or any mixture thereof; and
x is ≤1, and
hexagonal ferrites of formula (IV):

$$MFe_6O_{19} \quad (IV),$$

wherein M is Ca, Sr, Ba, and combinations thereof.

10. The mixture according to claim 1, wherein the magnetic iron oxide particle has a particle size in the range from 500 nm to 10 μm.

11. The mixture according to claim 1, wherein the magnetic iron oxide particle comprises the cubic ferrite of formula (III):

$$M^{2+}_x Fe^{2+}_{1-x} Fe^{3+}_2 O_4 \quad (III),$$

wherein:
M is Co, Ni, Mn, Zn or any mixture thereof; and
x is from greater than 0 to ≤1.

12. The mixture according to claim 1, wherein the magnetic iron oxide particle comprises the hexagonal ferrite of formula (IV):

$$MFe_6O_{19} \quad (IV),$$

wherein M is Ca, Sr, Ba, and combinations thereof.

* * * * *